United States Patent [19]
Bermas

[11] Patent Number: 5,468,447
[45] Date of Patent: Nov. 21, 1995

[54] REFRIGERATOR FRESHENER

[75] Inventor: Edward M. Bermas, Greenwich, Conn.

[73] Assignee: Harrison-Clifton Inc., Greenwich, Conn.

[21] Appl. No.: 354,935

[22] Filed: Dec. 13, 1994

Related U.S. Application Data

[63] Continuation of Ser. No. 159,732, Nov. 30, 1993, abandoned.

[51] Int. Cl.$^6$ .................................................... A61L 9/00
[52] U.S. Cl. ...................... 422/5; 422/1; 422/4; 422/120; 422/122
[58] Field of Search ........................... 422/1, 5, 4, 120, 422/122; 239/34, 57, 43

[56] References Cited

U.S. PATENT DOCUMENTS

| | | | |
|---|---|---|---|
| 1,737,532 | 11/1929 | Allen | 422/5 X |
| 1,954,893 | 4/1934 | Saeks | 422/5 X |
| 2,085,991 | 7/1937 | Minot | 422/5 X |
| 2,206,705 | 7/1940 | Newman | 422/5 X |
| 3,990,872 | 11/1976 | Cullen | 55/274 |
| 4,401,447 | 8/1983 | Huber | 55/387 |
| 4,402,717 | 9/1983 | Izumo et al. | 55/388 |
| 4,437,429 | 3/1984 | Goldstein et al. | 119/1 |
| 4,534,775 | 8/1985 | Frazier | 55/74 |
| 4,604,110 | 8/1986 | Frazier | 55/74 |
| 4,795,482 | 1/1989 | Giofree et al. | 55/75 |
| 4,826,497 | 5/1989 | Marcus et al. | 55/75 |
| 5,019,254 | 5/1991 | Abrevaya et al. | 210/169 |
| 5,087,273 | 2/1992 | Ward | 55/279 |
| 5,224,975 | 7/1993 | Purnell et al. | 55/389 |
| 5,304,358 | 4/1994 | Hoyt et al. | 422/5 X |

Primary Examiner—Robert J. Warden
Assistant Examiner—Krisanne M. Thornton
Attorney, Agent, or Firm—St. Onge Steward Johnston & Reens

[57] ABSTRACT

A refrigerator freshening device includes an air-permeable container, enclosing a mixture, in particulate form, of a major amount of activated carbon and a minor amount of an odor-absorbing zeolite. The activated carbon is preferably characterized by a good distribution of large and small pores, at least 30 percent of the pores having a diameter of from about 15 to less than about 50 Å and the zeolite by a strong organophilic character and a surface area of at least about 400 square meters per gram. The combination of particulate adsorbent materials preferably includes from about 5 to about 25 percent of the zeolite and from about 75 to about 95 percent of the activated carbon. The device preferably includes a front panel, a back panel, and a package constructed of flexible, porous material enclosing absorbent, wherein the front panel receives the back panel in nesting relationship and encloses the package of adsorbent material. Hooks are preferred to suspend the device freely within a refrigerator. The device maintains a fresh environment within a refrigerator, by acting immediately to delay the buildup of odors when aromatic foods are placed therein and continues to maintain low odor levels for extended times.

4 Claims, 2 Drawing Sheets

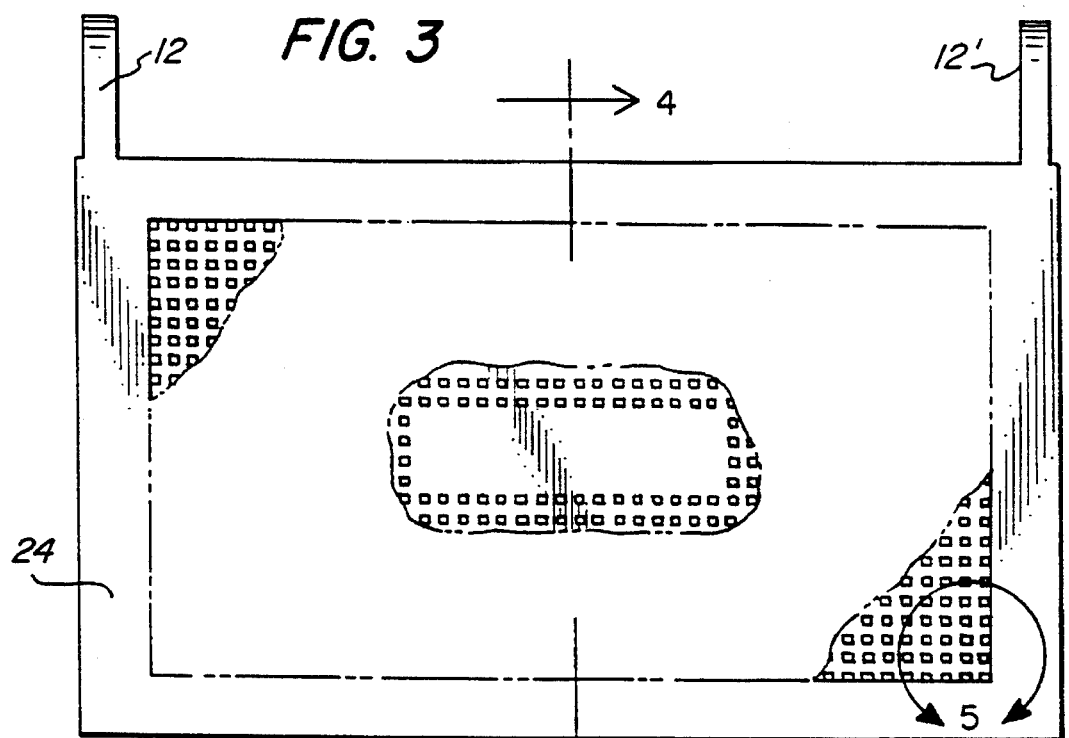
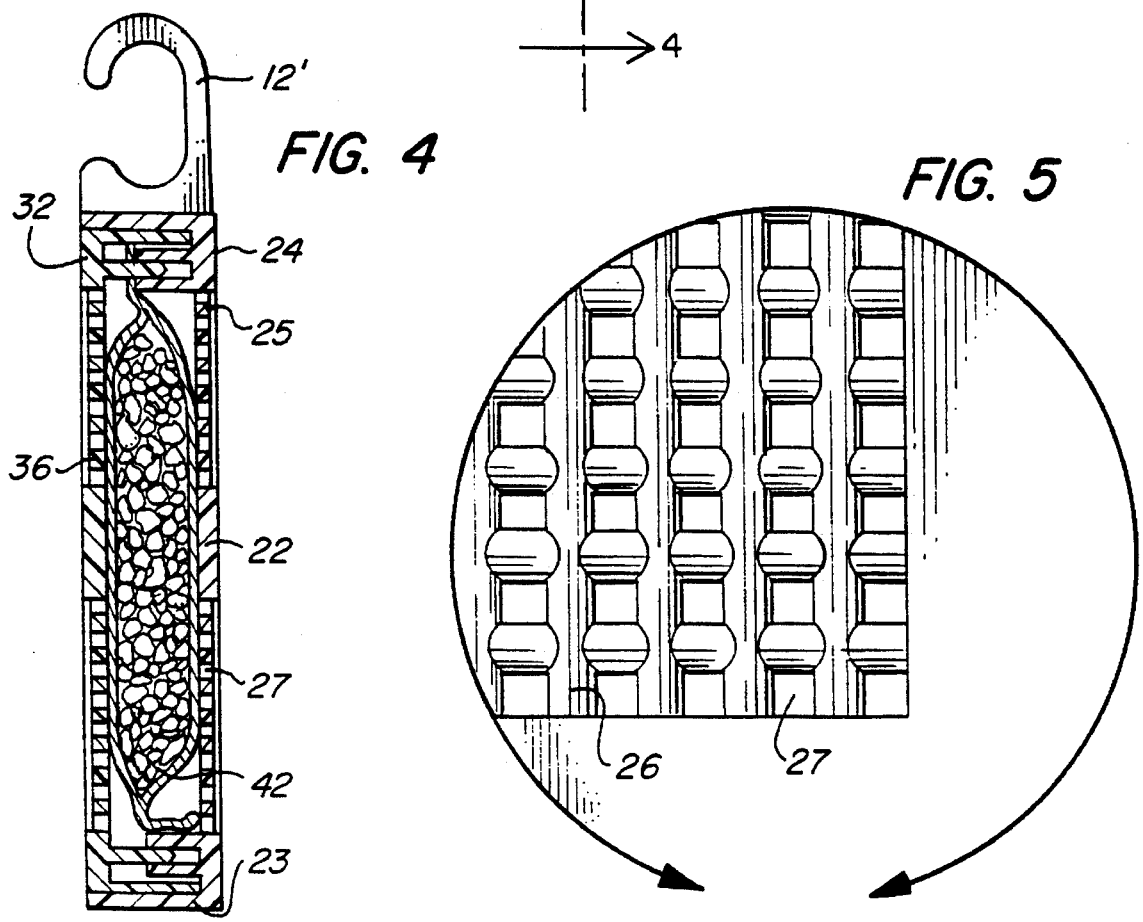

REFRIGERATOR FRESHENER

This is a continuation of copending application(s) Ser. No. 08/159,732 filed on Nov. 30, 1993, now abandoned.

TECHNICAL FIELD

The invention relates to an improved device for maintaining a fresh environment within a refrigerator, and especially to one which acts immediately to delay the buildup of odors when aromatic foods are placed therein and continues to maintain low odor levels for extended time periods.

The odors of various foods, such as onion, garlic, strong cheeses, gamey meats, and the like, often fill the refrigerator with a bouquet of strong and incompatible aromas. This presents the home cook with a problem—beyond mere unpleasantness—of the blending of odors and flavors among the various foods stored in the refrigerator. Long term storage is certainly a problem, but one particularly troublesome situation is the short term storage of foods prepared in advance of or brought to a dinner party or other social gathering. The desirable aroma of one dish can, by sharing its essence, diminish the character of another food.

Many techniques have been employed over the years to reduce the problem, and the most important of these is simply to use care when wrapping foods for refrigerator storage. However, even with care, some odors are just too strong to deal with and something more than discretion is required. Other techniques have employed various odor eaters, such as baking soda, active carbon, certain zeolites, and the like. Each of these seems to provide some help, but there remains a need for a device and a technique that can moderate the level of odor initially as well as over time.

Background Art

The art of fresheners for refrigerators is unique to itself because of the wide variety of strong odors that are typically involved and the effect that they can have on the foods stored. This is clearly different from the art of air fresheners in general which often remove only certain types of odors or try to cover up some with others—perfumes and fragrances, no matter how pleasant, can't be employed. The additive effect of these materials with the naturally evolved odors from the contents of the refrigerator, will not necessarily be pleasant. Moreover, such additives can alter the desired flavor and aroma of stored materials. For refrigerators, odor controllers typically employ absorbent or adsorbent materials such as baking soda ($NaHCO_3$), activated carbon, zeolites, clays and other minerals, and the like. Combinations of various of these materials have also been used for specified purposes, but no combination has been known to provide the desired short term and long term effects.

In U.S. Pat. No. 3,990,872, Cullen describes an absorbent package made of spunbonded olefin walls holding a particulate adsorbent material. The adsorbent materials identified are silica gel, activated carbon, bentonite, montmorillonite, molecular sieve, and any other type of desiccant or adsorbent material desired. No direction is given for refrigerator use.

U.S. Pat. No. 4,401,447, to Huber describes an adsorbent unit for use internally of a refrigerant system, but not a refrigerator per se. This patent also provides a wide variety of choices for adsorbents with no particular preference for any. The absorbent may selectively include, without limitation, adsorbents such as silica gel, metal, alumino silicate, alumina, calcium sulfate, activated charcoal, molecular sieve, or any other desired compound in bead, pellet or granular form.

In U.S. Pat. No. 4,437,429, Goldstein et al. disclose, not a refrigerator freshener, but a litter for cats or other small animals. Their composition of a zeolite, such as clinoptilolite, in combination with a clay or other sorptive, noncolloidal granular aluminosilicate, is said to have extended life as compared to litters made of clay alone.

In U.S. Pat. No. 4,534,775 and its divisional U.S. Pat. No. 4,604,110, Frazier describes an air filter element—of the type typically referred to as a room air freshener—for use with a fan for drawing room air though it to remove odors. The filter element includes a dry mixture of silica gel, activated carbon, and a zeolite, all preferably in particulate form, packed into a filter body so as to minimize the pore volume or void space. The dry mixture can be impregnated with a liquid for inhibiting the growth of microorganisms. While each of the components of the dry mixture is disclosed to be used at a level of from about 10 to 80 weight percent, it is preferred to employ essentially equal weights of each. The patentee discloses that the materials together synergistically remove a wide spectrum of household odors.

In U.S. Pat. No. 4,795,482, Gioffre et al. describe reducing odors attributable to organic molecular species, through the use of a crystalline molecular sieve material having at least 90% of its tetrahedral oxide units as $SiO_2$ tetrahedra, having pore apertures nominally at least 5.5 Å in diameter, and meeting other criteria. This class of materials is said to include zeolites as well as the so-called silica polymorphs. Comparisons are cited between these molecular sieves (exemplified as zeolites), activated charcoal, silicalite, silica gel, $NaHCO_3$, and mixtures of the zeolite with silicalite. Combinations of charcoal and zeolite were not tested.

In U.S. Pat. No. 4,826,497, Marcus et al. disclose a fibrous absorbent article (disposable diapers, catamenial devices, wound dressings, etc.) containing a suitable zeolite having the ability to deodorize with respect to bodily fluids, even in the presence of water. Comparisons are made between several zeolites, activated charcoal, silica gel, silicalite, $NaHCO_3$, and various combinations other than the combination of activated charcoal and zeolite.

Thus, despite the wide range of prior art describing and comparing various gas adsorbing materials for use in various deodorizing situations, it has not been previously recognized that combinations of crystalline aluminosilicate zeolite adsorbents, in minor amount, with a major amount of activated charcoal, would have particular utility for a refrigerator freshener—particularly one which fills the need for rapid response in combination with long acting odor reduction.

BRIEF DESCRIPTION OF THE DRAWINGS

The invention will be better understood and its advantages will be better appreciated from the following detailed description, especially when read in connection with the accompanying drawings, wherein:

FIG. 3 is a front elevational view of the refrigerator freshener shown in FIG. 2;

FIG. 4 is a cross-sectional view of a preferred form of refrigerator freshener of the invention, taken along line 4—4 in FIG. 3; and FIG. 5 is an enlarged view of detail of the refrigerator freshener shown in FIG. 3.

Disclosure of the Invention

It is an object of the invention to provide an improved device for maintaining the freshness of the air within a refrigerator.

It is another object of the invention to provide an improved device for maintaining the freshness of the air within a refrigerator by immediately eliminating odors to prevent their buildup after placing odorous foods in the refrigerator.

It is a more specific object of the invention to provide an improved device for maintaining the freshness of the air within a refrigerator, especially shortly after placing therein highly odorous foods, such as onion, garlic, strong cheeses, aged meats, and the like.

It is yet another object of the invention to provide a device and a technique for its use which can moderate the level of odor in a refrigerator both when storing foods both initially and over extended times.

These and other objects are realized by the present invention which provides both a device and a technique for its use which can moderate the level of odor initially as well as over time. The device, in one of its broader aspects comprises an air-permeable container enclosing a mixture, in particulate form, of a major amount of active carbon and a minor amount of an odor-absorbing zeolite. The technique or process of the invention comprises suspending the container, as described above, from a refrigerator shelf to permit the normal movement of air within the refrigerator to pass by and be deodorized by the active carbon and the zeolite.

The combination of particulate adsorbent materials preferably includes from about 5 to about 25 percent of the zeolite and from about 75 to about 95 percent of the activated carbon. Unless otherwise indicated, all parts and percentages used in the specification, are based on the weight of the ingredient or material at the indicated stage of processing.

The device preferably includes a front panel a back panel, and a package constructed of flexible, porous material enclosing absorbent, wherein the front panel receives the back panel in nesting relationship and encloses the package of adsorbent material. Hooks are preferred to suspend the device freely within a refrigerator.

Industrial Applicability

Figure 1:
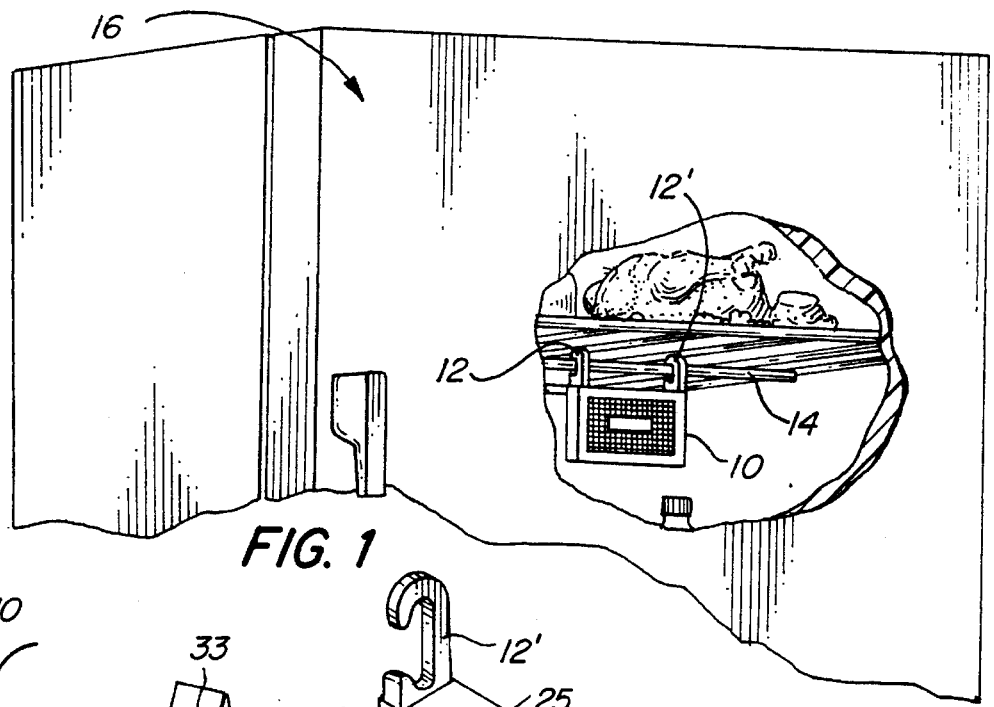
FIG. 1 is a perspective view of a preferred form of air freshener of the invention freely hanging within a refrigerator compartment.

The invention will be described below with specific reference to a preferred embodiment as illustrated in FIGS. 1 through 5. The refrigerator freshening device 10 of the invention preferably includes hooks 12 and 12' to facilitate hanging it from a wire shelf element 14 in a refrigerator 16 as shown in FIG. 1.

The ability to freely suspend the device 10 in this manner permits a free circulation of air around and into contact with it by maintaining it in a position off of the storage surfaces. The device 10 permits bulk flow of air within the refrigerator 16 to come into contact with it at a sufficient rate and for a sufficient time period to immediately have a significant odor reducing effect on odors emanating from foods. Accordingly, when a variety of foods are prepared ahead of time for an event and placed in the refrigerator, the refrigerator freshening device of the invention will help each food maintain its own natural flavor and aroma, unadulterated by the odors of the other foods.

Figure 2:
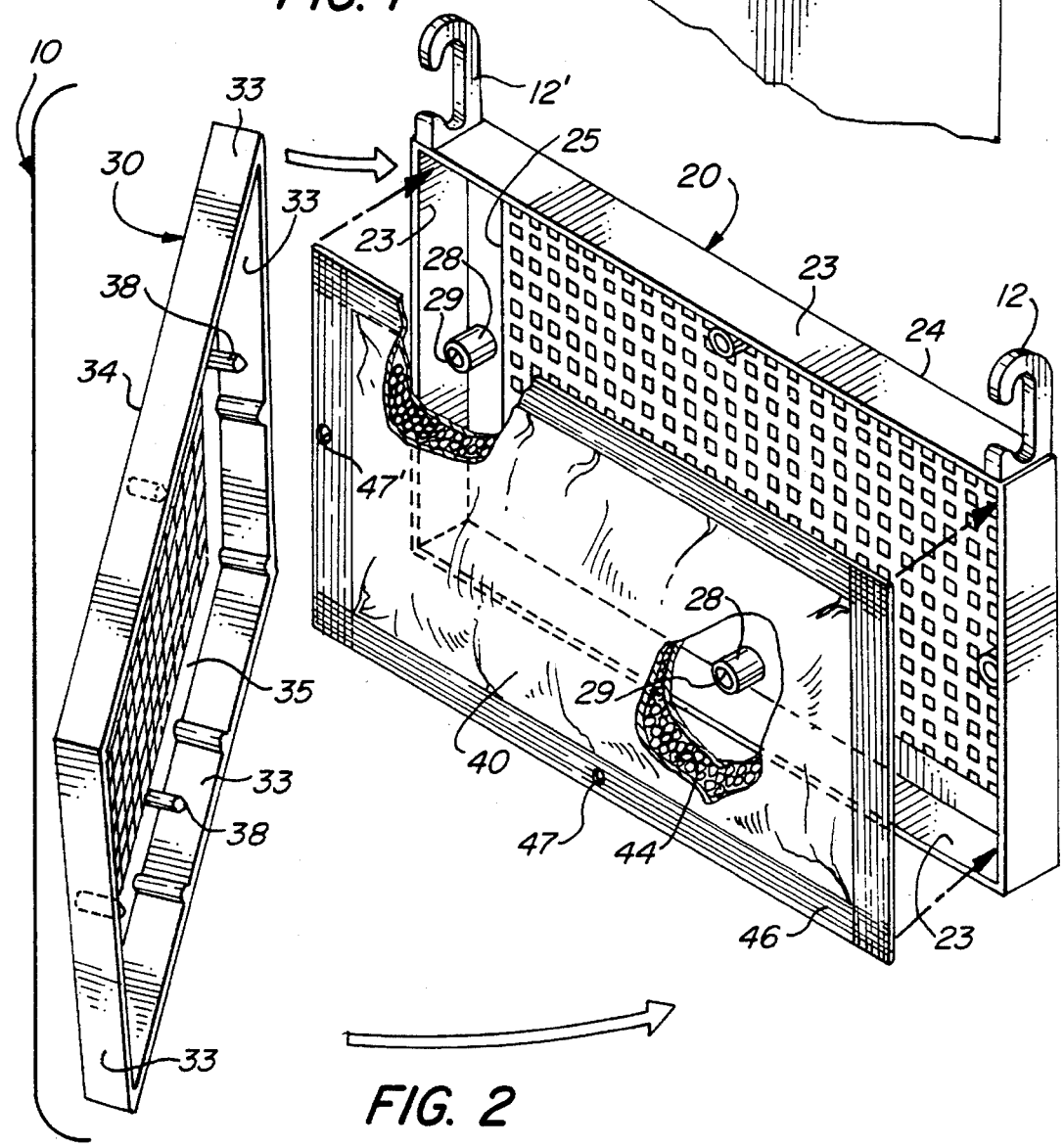
FIG. 2 is an exploded perspective view, partially cut away, showing a preferred form of refrigerator freshener of the invention.

FIG. 2 is an exploded view showing the principal structural features of the refrigerator freshener of the invention. A front panel 20 receives back panel 30 in nesting relationship, enclosing absorbent package 40.

The front panel 20 includes a rectangular front wall member 22 (see FIG. 4), and four side wall members 23. The front wall member has an outside surface 24 (see FIGS. 3 and 4) and an inside surface 25. The detail of FIG. 5 shows the grid structure provided by ribs 26 and holes 27 which extend through the front wall member from the inside surface to the outside surface. Extending outwardly from the inside surface, and positioned near each of the side wall members 23, are posts 28 having holes 29 therein. As will be explained below, the posts function with the package 40 and complimentary means on the back panel to suspend the package.

The back panel 30 includes a rectangular rear wall member 32, and four side wall members 33. The rear wall member has an outside surface 34 (see FIG. 4) and an inside surface 35 with a grid structure 36 which is similar in structure to that of the front panel. Posts 38 extend outwardly from the inside surface 35 of back panel 30. The posts 38 are located at suitable positions to enable engagement with the holes 29 in posts 28 on the front wall member. The posts 38 should be of similar diameter as the holes, optionally with a slight taper or other means facilitating mechanical or frictional interlock, to permit a secure fit. The outer dimension of the rear panel 30 is defined by wall members 33 and is selected to nest within the opening defined by the wall members 23 of the front panel 20. It will be apparent, however, that the post and wall panel dimensions can be varied as desired to achieve the necessary structural integrity of the unit with the package 40 suspended between the porous front and rear panel members.

The package 40 includes a porous outer wall member 42 which encloses a granular adsorbent 44 composition which comprises a major amount of activated carbon and a minor amount of zeolite. Preferably, the porous outer wall member should have a porosity at least sufficient to permit refrigerator air to freely flow into and out of the package but not so great as to permit dust from the particulate adsorbents to escape through the pores. Preferably, the permeability will be within the range of up to about 100 gurley seconds, e.g. from about 5 to about 25 gurley seconds.

In practice, porous paper and nonwoven polymeric felt materials such as employed for teabags, coffee filters, and as specifically available for use in making pouches for odor adsorbents, can be employed. A preferred material is made of a nonwoven fabric comprised of polyester and polypropylene, e.g. at a ratio of 63.3 parts polyester to 36.7 parts of the polypropylene. The package shown in the drawing is made by cutting two thicknesses of a heat-sealable nonwoven fabric, which is sealed around the entire periphery to enclose particulate adsorbent 44 and provide a compressed marginal edge 46. Holes as needed, e.g. 47 and 47', can be provided to suspend the package from posts 28 between the front and rear panels.

The surprisingly good combination of effectiveness for initial response to strong odors and extended effectiveness against accumulating odors achieved by the refrigerator freshener of the invention is believed due to the combination of the activated carbon and the zeolite. The loose packing of the particulate materials in the package 40, its suspension between the porous front and rear wall members 22 and 32, and the suspension of the device by hooks 12 and 12' in the freely circulating air in a refrigerator enhance this effectiveness. Preferably, the particulate materials will have a bulk density of from about 0.3 to about 0.6 grams per cubic centimeter.

Preferred forms of activated carbon are characterized by a good distribution of large and small pores, preferably with at least 30 percent of the pores having a diameter of from about 15 to less than about 50 Å, most preferably from about 15 to about 20 Å, and one preferred form is available from Calgon as BPL 6×16 granular carbon.

Preferred forms of zeolite are characterized by a strong organophilic character and a surface area of at least about 400 square meters per gram, and one preferred form is available from UOP as Abscents® deodorizing powders. In general, the preferred zeolites are those crystalline molecular sieve materials having at least 90% of their tetrahedral oxide units as $SiO_2$ tetrahedra, and having pore apertures nominally at least 5.5 Å in diameter, such as described in the abovementioned U.S. Pat. No. 4,795,482, which is hereby incorporated in its entirety.

Preferred combinations of these granular adsorbent materials will consist essentially of a zeolite and activated carbon, including from about 5 to about 25 percent of the zeolite and from about 75 to about 95 percent of the activated carbon. The most preferred combinations will contain from about 7 to about 15 percent of the zeolite, e.g. about 9 percent, with from about 85 to about 93 percent of the activated carbon.

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is defined by the following claims. The claims are meant to cover the indicated elements and steps in any arrangement or sequence which is effective to meet the objectives intended for the invention, unless the context specifically indicates the contrary.

I claim:

1. A refrigerator freshening device which is capable of suspension from a wire rack in a refrigerator, is effective to reduce the level of food odor in the refrigerator, and comprises:

a front panel including a rectangular front wall member and four side wall members, the front wall member having an outside surface, an inside surface, and a grid structure including holes which extend through the front wall member from the inside surface to the outside surface;

a back panel, including a rectangular rear wall member and four side wall members, the rear wall member having an outside surface, an inside surface, and a grid structure including holes which extend through the rear wall member from the inside surface to the outside surface;

a package constructed of flexible, porous material enclosing an absorbent, in particulate form, consisting essentially of from 75 to 95 percent of active carbon having pores wherein at least 30 percent of the pores have a diameter of from about 15 to less than about 50 Å and from 5 to 25 percent of an odor-absorbing zeolite having an organophilic character and a surface area of at least 400 square meters per gram;

wherein the front panel receives the back panel in nesting relationship and encloses the package of adsorbent material; and at least one hook is provided to enable suspension of the device from a refrigerator shelf.

2. A refrigerator freshening device according to claim 1, wherein the absorbent includes from about 7 to about 15 percent of the zeolite.

3. A process for maintaining a fresh environment within a refrigerator, by acting immediately to delay the buildup of odors when aromatic foods are placed therein and continuing to maintain low odor levels for extended times, comprising:

providing a refrigerator freshening device which is capable of suspension from a wire rack in a refrigerator, is effective to reduce the level of food odor in the refrigerator, and comprises a front panel including a front wall member and side wall members, the front wall member having an outside surface, an inside surface, and a grid structure including holes which extend through the front wall member from the inside surface to the outside surface;

a back panel, including a rear wall member and side wall members, the rear wall member having an outside surface, an inside surface, and a grid structure including holes which extend through the rear wall member from the inside surface to the outside surface;

a package constructed of flexible, porous material enclosing an absorbent, in particulate form, consisting essentially of from 75 to 95 percent of active carbon having pores wherein at least 30 percent of the pores have a diameter of from about 15 to less than about 50 Å and from 5 to 25 percent of an odor-absorbing zeolite having an organophilic character and a surface area of at least 400 square meters per gram wherein the front panel receives the back panel in nesting relation ship and encloses the package of adsorbent material; and at least one hook is provided to enable suspension of the device from a refrigerator shelf; and suspending the container from a refrigerator shelf to permit the normal movement of air within the refrigerator to pass by and be deodorized by the active carbon and the zeolite.

4. A process according to claim 3, wherein the combination of particulate absorbent materials consists essentially of a zeolite and activated carbon, including 7 to about 15 percent of the zeolite.

\* \* \* \* \*